(12) United States Patent
Banda et al.

(10) Patent No.: US 6,626,026 B2
(45) Date of Patent: Sep. 30, 2003

(54) ACOUSTIC WAVE BASED SENSOR

(75) Inventors: Pedro Banda, Kessel-lo (BE); Andrew Campitelli, Leuven (BE)

(73) Assignee: Interuniversitair Microelektronica Centrum (IMEC), Leuven (BE)

( * ) Notice: Subject to any disclaimer, the term of this patent is extended or adjusted under 35 U.S.C. 154(b) by 17 days.

(21) Appl. No.: 09/828,449

(22) Filed: Apr. 6, 2001

(65) Prior Publication Data

US 2001/0054305 A1 Dec. 27, 2001

Related U.S. Application Data

(60) Provisional application No. 60/195,530, filed on Apr. 7, 2000.

(51) Int. Cl.[7] ......................... H01L 41/08; G01F 17/00; G01N 9/24
(52) U.S. Cl. ......................... 73/24.01; 73/61.75; 73/592; 73/24.06
(58) Field of Search ............................ 73/24.01, 24.03, 73/24.06, 61.58, 61.75, 661, 592

(56) References Cited

U.S. PATENT DOCUMENTS

| | | | |
|---|---|---|---|
| 4,312,228 A | 1/1982 | Wohltjen | 73/597 |
| 4,361,026 A | 11/1982 | Muller et al. | 73/23 |
| 5,054,490 A * | 10/1991 | Rossman et al. | 128/661.03 |
| 5,129,262 A | 7/1992 | White et al. | 73/599 |
| 5,189,914 A | 3/1993 | White et al. | 73/599 |
| 5,212,988 A | 5/1993 | White et al. | 73/599 |
| 5,247,826 A * | 9/1993 | Frola et al. | 73/24.01 |
| 5,283,037 A | 2/1994 | Baer et al. | 422/82.01 |
| 5,306,644 A | 4/1994 | Myerholtz et al. | 436/149 |
| 5,321,331 A * | 6/1994 | Baer et al. | 310/313 D |
| 5,668,303 A * | 9/1997 | Giesler et al. | 73/24.06 |
| 5,729,207 A * | 3/1998 | Yamano | 340/628 |
| 5,768,937 A * | 6/1998 | Wajid et al. | 73/24.06 |
| 5,795,993 A * | 8/1998 | Pfeifer et al. | 73/24.01 |
| 5,817,921 A * | 10/1998 | Tom et al. | 73/24.01 |

FOREIGN PATENT DOCUMENTS

| | | |
|---|---|---|
| EP | 0 542 469 A1 | 11/1992 |
| JP | 05-240762 | 9/1993 |
| WO | WO 89/08336 | 9/1989 |

\* cited by examiner

*Primary Examiner*—Helen Kwok
*Assistant Examiner*—David J. Wiggins
(74) *Attorney, Agent, or Firm*—Knobbe, Martens, Olson & Bear LLP

(57) ABSTRACT

An apparatus that is configured to sense the presence of gases, vapors and liquids using acoustic waves. The apparatus comprises a first part that is configured to generate acoustic waves. The apparatus further comprises a second part having a sensing and acoustic wave guiding device, which is configured to sense the presence of such substances and propagate acoustic waves. The first part is removably fixable to the second part of the apparatus. When the first part is fixed to the second part, the acoustic waves propagate in the second part.

15 Claims, 4 Drawing Sheets

ACOUSTIC WAVE BASED SENSOR

This application claims the benefit of U.S. Provisional Application Ser. No. 60/195,530, filed Apr. 7, 2000.

BACKGROUND OF THE INVENTION

There is a considerable interest in methods and apparatus for detection, measuring and monitoring chemical properties of a substance. Apparatus for detecting the presence of a substance based on the detection of acoustic waves have received increasing interest in recent years in a wide range of applications. They can, for example be used as resonators, filters, sensors and actuators.

Experimental configurations have relied on expensive commercial test equipment such as spectrum/network analyzers, fixed oscillators and vector voltmeters. Together with this, separate liquid flow systems requiring external computer control, restrict the experiment environment and impose specialized experimental test procedures. The development of a fully portable, stand alone acoustic wave (AW) sensor system that encompasses both the sensor data acquisition and liquid flow systems is seen as a positive and exciting advancement in the development of AW sensors. However, the majority of reported work to date on AW sensors has ignored the optimization of the overall sensor configurations for the development of portable instrumentation for the detection of very low concentrations of target analyte.

U.S. Pat. No. 4,361,026 describes a method and an apparatus for sensing fluids using acoustic waves. The apparatus describes a completely integrated sensor. A disadvantage of this sensor is the high manufacturing cost of the sensor. In, for example, medical applications, one is mostly interested in single-use devices. Moreover, the '026 patent does not allow for quick changes in the sensor geometry without changing the overall sensor configuration.

This will result in a high cost for each sensor. The sensor described in the '026 patent is based on a standard SAW delay line onto which a sensitive and selective film is deposited. The design is intended to work at the design frequency exclusively, and no disposability has been contemplated. Furtheron, the sensor is based on surface acoustic modes exclusively, which does not make multilayer propagation possible.

Another patent in the art is U.S. Pat. No. 4,312,228 which describes a method and an apparatus for the monitoring the physical parameters relating to various fluids and polymers based on acoustic waves. Physical parameters relating to fluids are investigated by contacting the fluid with a coating on the surface of a piezoelectric material unit. The coating on the piezoelectric substrate is selective to the interaction with the fluid to detect. The sensor is very bulky. The coating is applied directly on the piezoelectric substrate, resulting in a lower sensitivity towards the substance. The '228 patent has the same disadvantages as recited above and moreover, the piezoelectric substrate is coated directly with a selective film. This results in a lower sensitivity. The '228 patent is focused on the description of the liquid cell for the sample delivery.

The present invention is directed to overcome the above mentioned problems.

SUMMARY OF THE INVENTION

The aim of this invention is to provide an apparatus for sensing the presence of a substance. Another aim of the invention is to provide an apparatus for sensing the presence of a substance that can be manufactured easily, cheaply and single-use focused on a variety of substrates. Yet another aim of the invention is to provide an apparatus for sensing the presence of a substance that is low cost, h as a fast response, has a simple experimental procedure, is portable, is small in size and has a high sensitivity.

The apparatus comprises two parts which are removably fixable such that first part is in close contact with second part during the working of the device. In a first aspect of this invention, an apparatus is disclosed for detecting the presence of a substance using acoustic waves comprising a first part for generating acoustic waves and a second part comprising a sensing and acoustic wave guiding device for sensing said substance and for propagating said acoustic waves. Said sensing and acoustic wave guiding device can, but is not limited to, comprise a sensing layer for sensing said substance and an acoustic wave guiding layer for propagating said acoustic waves. Said sensing layer is for sensing said substance. Preferably said acoustic waves are surface acoustic waves. Acoustic wave guiding layer propagates said acoustic waves. In this first aspect of the invention, said first part is removably fixable to said second part so that when fixed said acoustic waves propagate in said second part. Said first part can contain, but is not limited to, a piezoelectric substrate. The acoustic wave guiding layer should be capable of supporting acoustic wave propagation. Besides this, the acoustic wave guiding layer is chosen such that it confines the acoustic waves energy at the sensor surface, rendering it highly sensitive to surface perturbations. In order for the acoustic energy to be confined in the guiding layer, it is preferable that the acoustic velocity for the material of the guiding layer be smaller than the acoustic velocity for the substrate. By selecting the appropriate acoustic wave guiding layer, very low perturbations at the surface of the sensing layer can be detected. The sensing layer can be, but is not limited hereto, directly applied on the acoustic wave guiding layer. Said first part is reusable, while said second part can be chosen depending on the substance to be detected. Said second part can be manufactured easily, cheaply and single-use and is preferably made from materials which are less expensive.

In a further embodiment, said sensing and acoustic wave guiding device propagates said acoustic waves for sensing said substance. This means that a part of said guiding layer is exposed to the substance and is able to interact with the substance.

In a further embodiment of this invention, an apparatus as recited in the first aspect of the invention is disclosed wherein said first part comprises at least a piezoelectric material.

In a further embodiment, an apparatus for detecting the presence of a substance as described in the first aspect of this invention is disclosed, wherein said apparatus further comprises an electrode layer. Said electrode layer is located on said second part. Said electrode layer can be embedded in said acoustic wave guiding layer. Preferably, the electrode layer has an interdigital configuration (IDT). When the electrode layer is located on the second part, it allows for quick changes in the design of the IDTs, as they are printed on the disposable part. It also allows for changes on the frequency of operation, since the frequency is determined by the geometry of the interdigital transducers.

In an alternative embodiment, said electrode layer can be embedded in said first part.

In a further embodiment of the invention, said second part of the apparatus can further comprise a support structure located at least on top of the sensing and acoustic wave guiding device. At least a part of the sensing and acoustic wave guiding device is exposed to the substance. The support structure can be made of a material selected from the group comprising a semiconducting material, a polymer based material or an amorphous material such as glass.

In a further embodiment of the invention, said sensing layer consists essentially of a recognition layer that may be influenced by interaction with said substance. The interaction can be a chemical or a physical interaction.

In a further embodiment of the invention, said acoustic wave sensor is designed such that the acoustic waves penetrate the sensing and acoustic wave guiding device in the region where the substance interacts with said sensing and acoustic wave guiding device, such that a perturbation of the acoustic waves due to the interaction of the substance with the sensing and acoustic wave guiding device, is obtained.

In a further embodiment of this invention, said apparatus further comprises a radio frequency (RF) generator for applying an input RF signal to said electrode layer and a receiver that receives an output RF signal from said electrode layer.

In a further embodiment, said apparatus further comprises a clamping system for removably fixing said first part to said second part. Said clamping system is chosen such that the propagation of the acoustic waves from the first part to the second part is not altered.

As some of the piezoelectric substrates are used also for optical and temperature applications, such substrate also allows for the integration of various sensors on the same first part of the apparatus.

BRIEF DESCRIPTION OF THE DRAWINGS

These and other features will now be described with reference to the drawings summarized below, These drawings and the associated description are provided to illustrate a preferred embodiment of the invention, and not to limit the scope of the invention.

DETAILED DESCRIPTION OF THE INVENTION

In relation to the appended drawings the present invention is described in detail in the sequel. Several embodiments are disclosed. It is apparent however that a person skilled in the art can identify several other equivalent embodiments or other ways of practicing the present invention, the spirit and scope thereof being limited only by the terms of the appended claims.

An apparatus for detecting the presence of a substance using acoustic waves is described. For the purpose of this invention, detecting the presence of a substance shall mean at least one of determining, identification, measuring concentrations or activities measuring a change of concentrations or activities of a substance. Particularly, the apparatus can be used for the detection of molecules in the substance in the biochemical and pharmaceutical field. Furthermore, the device can be used for the detection of substances contain specific analytes e.g. vapors, odors, gases. The device can further be used for detecting the influence of a physical stimulus such as, but not limited hereto, radiation or temperature on the sensing layer (or substances bound to the sensing layer).

Acoustic waves shall comprise, but is not limited to, various acoustic modes such as Love modes, Lamb waves, shear horizontal modes, Rayleigh waves, thickness modes.

Figure 1:
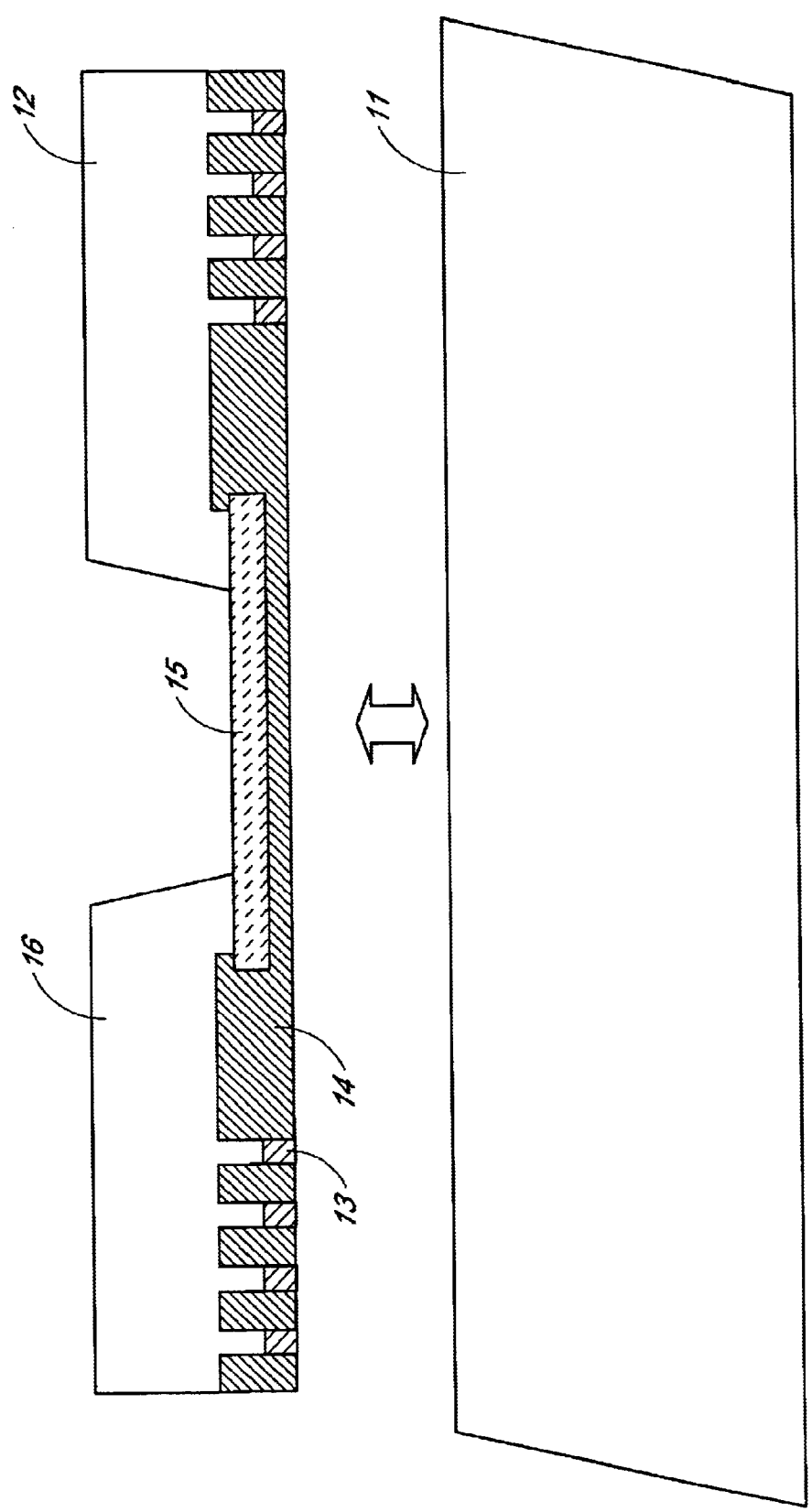
FIG. 1 shows an apparatus for detecting the presence of a substance using acoustic waves.

FIG. 1 shows an apparatus for detecting the presence of a substance using acoustic waves. The apparatus of FIG. 1 comprises a first part (11) for generating acoustic waves and a second part (12) comprising a sensing and acoustic wave guiding device for propagating said acoustic waves and for sensing said substance. The first part is removably fixable to said second part so that said acoustic waves propagate in said second part. The first part and second part of the apparatus can be fixed to each other by means of a clamping system. A clamping system can be a mechanical clamping system such as a jig force, a magnetic or electromagnetic clamping system or a vacuum system. A vacuum system and can be used to apply a vacuum between first part and second part such that both parts are in close contact. The vacuum system can further comprise a sealing element such as O-rings. It is preferable that the manner in which the contact is effected should not be destructive for the first part of the apparatus.

The generating of acoustic waves is achieved by applying of a voltage to the electrode layer (13) which is in direct or indirect contact with the first part of the apparatus. An electrical signal is converted into mechanical acoustic waves. Hereafter, acoustic waves are propagating in the first part of the apparatus and in the acoustic wave guiding layer(14). The propagation characteristics of the acoustic waves are altered by physical changes at the surface of the sensing layer (15). This perturbation can be caused by an interaction between the sensing layer and the substance, as a consequence, the perturbation depends on the chemical and physical characteristics of the substance and the sensing layer (15). A change in the velocity of the acoustic waves is detected. The electrode layer converts the altered mechanical characteristics of the acoustic wave (i.e the altered velocity) into an electrical signal. The altered electrical signal is a measure of the characterization of the substance.

After the measurement of the altered electrical signal, the first part and the second part can be disconnected and the first part can be reused in a further experiment while the second part is disposable.

In one embodiment of this invention, the apparatus comprises a first part for generating acoustic waves. This part can be, but is not limited to, a piezoelectric material, a layered structure comprising a thin film piezoelectric structure or a suspended structure of a piezoelectric or non piezoelectric material. The piezoelectric material can be a crystal die. The layered structure can be based on multilayered thin films which comprise materials such as ZnO, AlN, ZnO/Diamond, AlN/Diamond-like carbon film or a commercial crystalline material such as quartz, lithium niobate, lithium tantalate piezoelectric material.

The thickness of the film depends on the material properties as many different types of multilayered structures exists.

The second part comprises a sensing and acoustic wave guiding device. In one embodiment, the sensing and acoustic wave guiding device comprises a sensing layer and an acoustic wave guiding layer. The acoustic wave guiding layer is chosen such that it confines the acoustic wave energy at the sensor surface, rendering it highly sensitive to surface perturbations. The acoustic wave guiding layer should be capable of supporting acoustic wave propagation. Materials that can be used are dielectric thin films in which the acoustic velocity is less than the acoustic velocity of the substrate, such as silicon dioxide, silicon nitride, BCB, Teflon, poly-imides and other polymeric materials. The thickness of such layers can be between 0.01 $\mu$m and 1000 $\mu$m, between 0.1 $\mu$m and 100 $\mu$m and preferably between 1 $\mu$m and 10 $\mu$m. The optimization of the thickness range depends on the intrinsic properties of the materials used. The sensing layer comprises at least one layer which is exposed to the substance to be investigated. The sensing layer can be a layer with a specific recognition function towards the substance. Preferably, there is a molecular recognition between the sensing layer and the substance. For the purpose of this invention, substance refers to a gas, vapor, solid, solution or mixture of those comprising any chemical molecule, atom or ion. For biochemical applications, chemical molecule can be enzymes, immunochemicals, hormones and reducible gases. In addition, the sensing layer can be sensitive towards environmental changes such as temperature, pressure, and others. Any sensing layer known in the art can be used as the sensing layer.

In a further embodiment of the invention, said sensing and acoustic wave guiding device comprises an acoustic wave guiding layer. The sensing and acoustic wave guiding device is for propagating the acoustic waves and has a specific recognition function towards the substance. It is not necessary to have the apparatus include a sensing device in the form of a separate sensing layer. Hence, the sensing and acoustic wave guiding device can provide a sensing function. For example, the sensing and acoustic wave guiding device is chosen such that it is able to interact with the substance. On the other hand, the acoustic wave guiding layer can be modified on the part which will be in contact with the substance. This modification can be, but is not limited to, a chemical modification. Hence, a selective interaction between the sensing layer and the substance can be obtained. This will further alter the propagation characteristics of the acoustic waves.

The apparatus as described above may further comprise an electrode layer. The electrode layer may be located on the first part or on the second part of the apparatus. The electrode layer is chosen such that an electrical signal propagates in the layer. The electrode layer has preferably an interdigitated configuration. Preferably, the electrode layer comprises at least one pair of interdigitated electrodes (IDT). The electrode layer can comprise, but is not limited hereto, a pair of IDT as input electrodes and a pair of IDT as output electrodes. The electrode layer can be made of a variety of standard integrated circuit (IC) fabrication materials such as aluminum, tungsten, titanium nitride, copper or non standard ones such as a gold-chromium alloy. The thickness of the electrode layer can be between 1 nm and 1000 nm and between 50 nm and 100 nm. The electrode layer is connected with an RF circuit. When the electrode layer is located on the second part, it allows for quick changes in the design of the IDTs, as they are printed on the disposable part. It also allows for changes on the frequency of operation, since the frequency is determined by the geometry of the interdigital transducers. This is an valuable improvement compared to prior art sensors.

The connections to the RF circuit can be located on the first part of the sensor, on the second part of the sensor or on a separated third part.

The sensing and acoustic wave guiding device can be covered with a support structure such as a support layer, while the sensing and acoustic wave guiding device remains partly exposed such that there may be an interaction between the sensing and acoustic wave guiding device and the substrate. Alternatively, when the sensing and acoustic wave guiding device comprises a sensing layer and an acoustic wave guiding layer, the acoustic wave guiding layer can be covered with a support structure such as a support layer (16), while the sensing layer remains at least partly exposed, so that there is an interaction between the sensing layer and the substance. Preferably, the support structure covers a portion of the sensing layer, such that a sensing part remains exposed.

When the electrodes are located on the second part, the support structure preferably covers the electrode layer. A cavity is formed in the support structure, such that the sensing layer is at least partly exposed and can interact with the substance. Moreover, the delivery of the substance may be controlled by channels formed in the support structure. The delivery of the substance can also be controlled by an external delivery system. The support structure can cover the sensing layer such that this layer is shielded from hostile environment such as elevated temperatures, corrosive vapours and physical contact.

Figure 2:
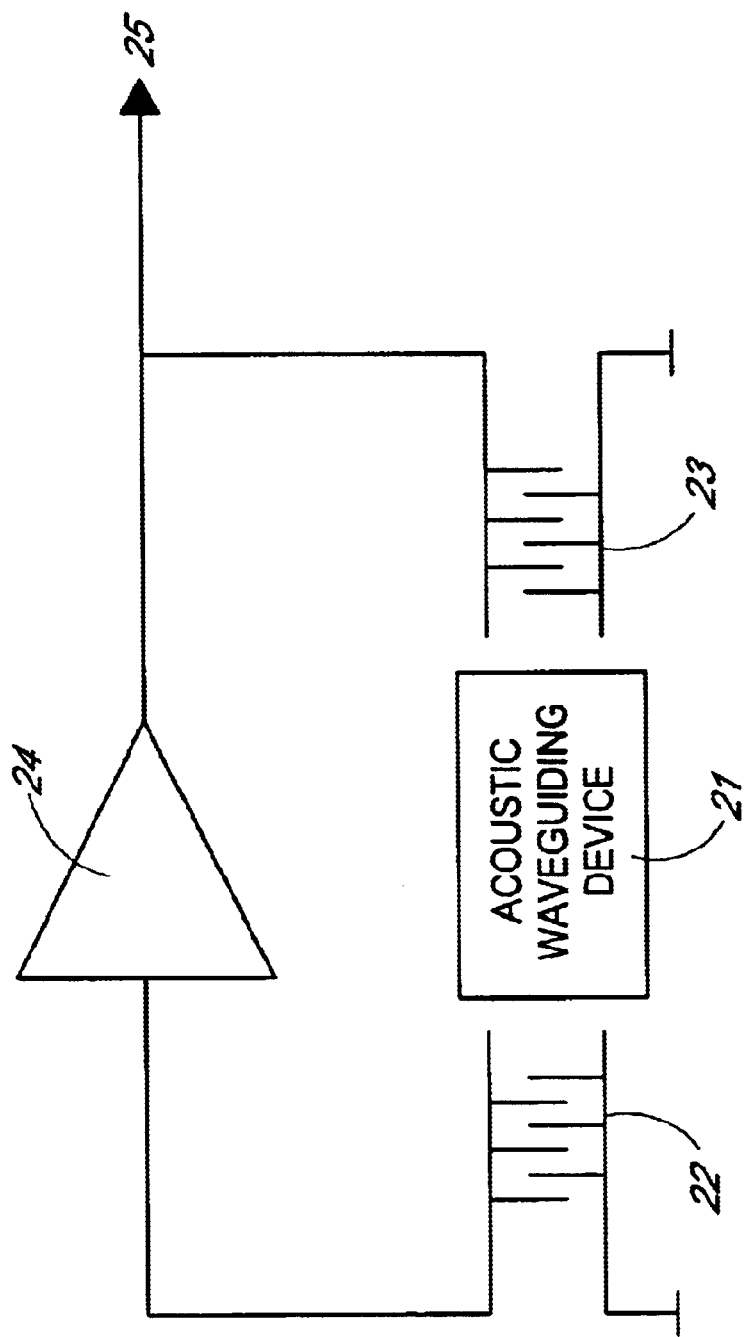
FIG. 2 shows a delay line oscillator configuration for the acoustic wave based sensor.

The apparatus as claimed in this invention can be part of an oscillation circuit. FIG. 2 shows a delay line oscillator configuration for the acoustic wave based sensor. The oscillation circuit comprises an input electrode layer (22), an output electrode layer (23), a sensing and acoustic wave guiding device (21), an RF amplifier (24) and means for detecting an output signal (25). The frequency of the oscillation circuit is determined by the geometry of the electrode layer and the propagation characteristics of the first part and the acoustic wave guiding layer.

The mass sensitivity of the AW sensor can be important. The mass detection limits of the apparatus as described in the invention may be between 0.01 ng/ml up to 100 ng/ml, and preferably below 1 ng/ml. This sensitivity can be achieved by the use of high resonant frequencies, preferably, but not limited, between 1 MHz and 10 GHz. The sensitivity can also be obtained by an optimization of the materials for the acoustic wave guiding layer.

The velocity of the acoustic waves is determined by the acoustic properties of the materials.

Figure 3:
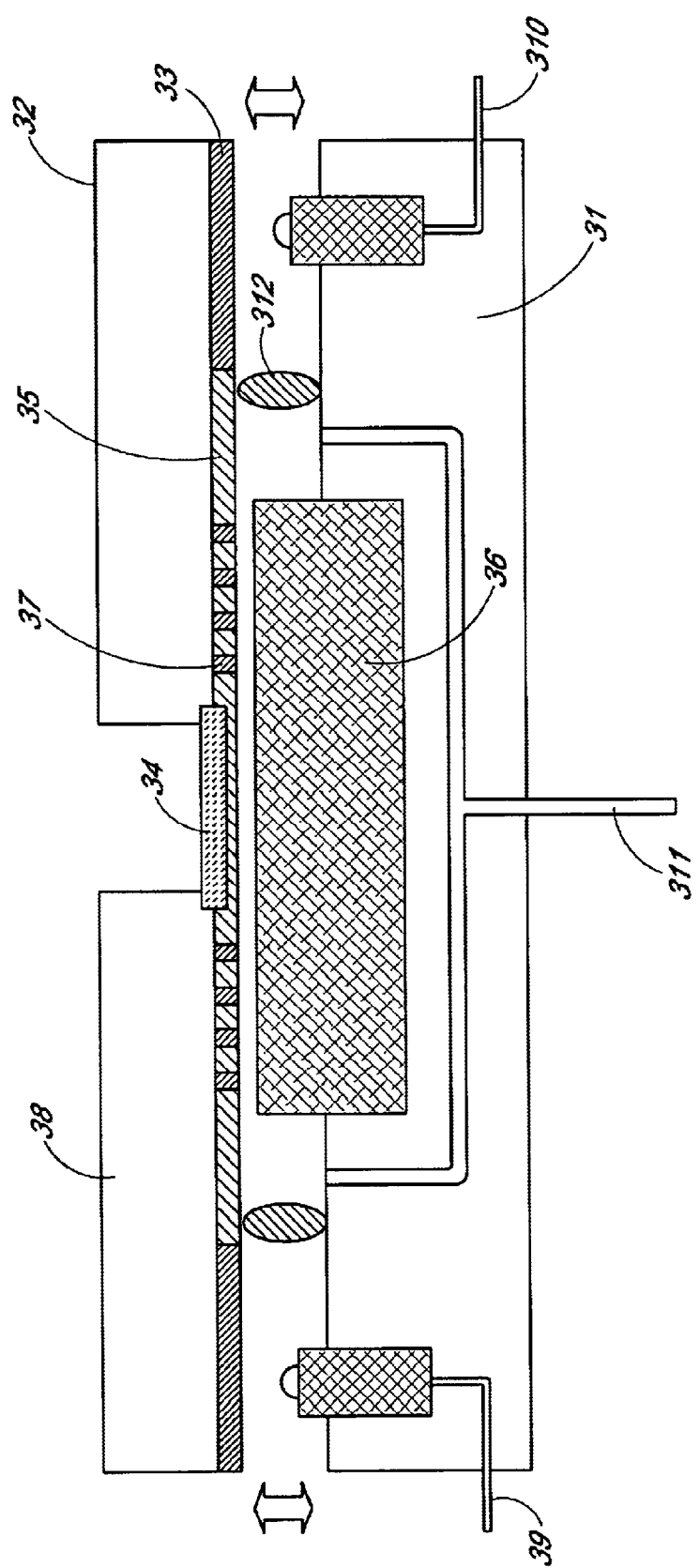
FIG. 3 shows a preferred embodiment of the acoustic wave based sensor.

FIG. 3 shows a preferred embodiment of the acoustic wave based sensor. In a preferred embodiment, an apparatus is disclosed for detecting the presence of a substance using acoustic waves comprising a first part (31) for generating acoustic waves and a second part (32) comprising a sensing and acoustic wave guiding device (33) for sensing said substance and for propagating said acoustic waves. Said sensing and acoustic wave guiding device comprises a sensing layer (34) for sensing said substance and an acoustic wave guiding layer (35) for propagating said acoustic waves. Said first part comprises a piezoelectric substrate (36).

Said apparatus further comprises an electrode layer (37) located the second part. The electrode layer has an interdigital configuration (IDT).

The second part (32) of the apparatus further comprises a support structure (38) located at least on top of the acoustic wave guiding layer (35). At least a part of the sensing layer (34) is exposed to the substance. The support structure (38) may be made of a material selected from the group comprising a semiconducting material, a polymer based material or an amorphous material such as glass. The apparatus further comprises an RF generator (39) for applying an input RF signal to the electrode layer (37), and a receiver (310) for receiving an output RF signal from the electrode layer (37). The apparatus further comprises a system (311) for applying a vacuum between the first and second part (31), (32), and a sealing element (312) such as O-rings for removably fixing the first part (31) to the second part (32).

The first part of the sensor can be manufactured by dicing and mounting. Preferably, no special fabrication process, apart from dicing and mounting is necessary. This part consists mainly of a piezoelectric substrate. If a piezoelectric thin film is used instead of a monocrystalline substrate, the fabrication process will include the thin film deposition by any standard technique such as, but not limited to physical or chemical vapor deposition, plasma-assisted deposition, spin-on or sol-gel.

Figure 4:
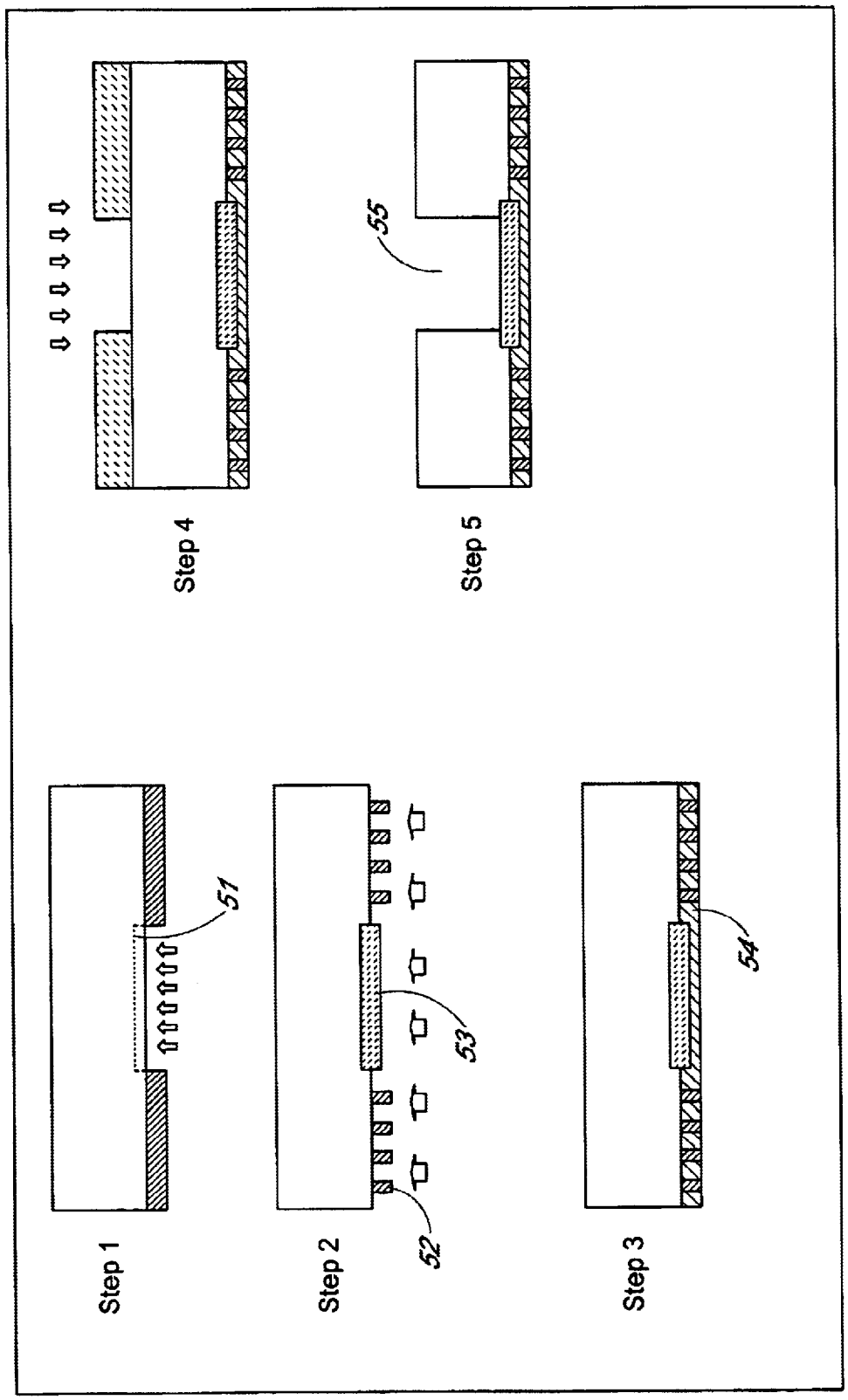
FIG. 4 shows a processing of the second part of the acoustic wave based sensor.

FIG. 4 shows a processing of the second part of the acoustic wave based sensor. The second part of the SAW sensor can be manufactured by double-sided processing (FIG. 4). The top side will be the side which is in contact with the sample side; the bottom side will be in contact with the first substrate.

The processing of the bottom side comprises the following steps:

Defining the sensing area (51) by vertical adjustment (step 1 of FIG. 4)

Depositing patterning the electrode layer for realization of the interdigital electrodes (52) (step 2 of FIG. 4).

Depositing and patterning the sensing layer (53) (step 2 of FIG. 4)

Depositing and patterning the acoustic wave guiding layer (54) (step 3 of FIG. 4).

The processing of the top side of the second part comprises patterning the sample well (55) (step 4 of FIG. 4). This process will be mainly etching through the support structure, such that the sensing area is exposed (step 5 of FIG. 4).

It should be understood that the processing sequence as described in this disclosure may be replaced by any processing sequence known in the art.

The apparatus as described in this invention may be used for many different applications. For example, it may be used as a biosensor, chemical vapor or gas detector, manometer or other pressure measuring device, a densitometer, a radiometer or a thermometer.

Apart from all sensing applications of the device, non-sensing applications can be contemplated as within the scope of the present invention.

The second part of the device can be used as a quick prototype tool that can be applied onto a variety of piezoelectric substrates (i.e., the first part of the device). Signal filtering for a wide range on frequencies as well as SAW based oscillators are some examples of the multiple signal processing applications.

What is claimed is:

1. An apparatus for detecting the presence of a substance using acoustic waves, the apparatus comprising:

a first part that is configured to generate acoustic waves; and a second part comprising a sensing and acoustic wave guiding device configured to sense said substance and propagate said acoustic waves, and further configured to confine said acoustic waves to a surface of said sensing and acoustic wave guiding device, and wherein said first part is removably fixable to said second part so that when fixed said acoustic waves propagate in said second part.

2. The apparatus as recited in claim 1 wherein said sensing and acoustic wave guiding device comprises a sensing layer for sensing said substance and an acoustic wave guiding layer for propagating said acoustic waves, respectively.

3. The acoustic wave sensor as described in claim 2 wherein said sensing layer comprises a recognition layer that is able to be influenced by interaction with said substance.

4. The apparatus as recited in claim 2 further comprising an electrode layer for propagating an electrical signal.

5. The apparatus as recited in claim 4 wherein said electrode layer is located on said second part.

6. The apparatus as recited in claim 5 wherein said electrode layer is embedded in said acoustic wave guiding layer.

7. The apparatus as recited in claim 4 wherein said electrode layer is located on said first part.

8. The apparatus as recited in claim 4 further comprising a support structure located on top of said electrode layer and acoustic wave guiding device while said sensing layer is exposed to the substance.

9. The apparatus as recited in claim 1 further comprising a support structure located on top of said sensing and acoustic wave guiding device while said sensing and acoustic wave guiding device remains partly exposed to the substance such that there is an interaction between the substance and the exposed part of said sensing and acoustic wave guiding device.

10. The apparatus as recited in claim 8 wherein said support structure is made of a material selected from the group comprising a semiconducting material or a polymer-based material.

11. The apparatus as recited in claim 1 wherein said acoustic wave penetrates the exposed part of said sensing and acoustic wave guiding device.

12. The apparatus sensor as recited in claim 1 wherein said first part comprises at least a piezoelectric material.

13. The apparatus as recited in claim 4 further comprising an RF generator that is configured to apply an input RF signal to said electrode layer and a receiver that is configured to receive an output RF signal from said electrode layer.

14. The apparatus as recited in claim 1 further comprising a clamp for removably fixing said first part to said second part.

15. The apparatus as recited in claim 14 wherein said clamp is one of the group comprising a vacuum pump or magnetic clamping system.

* * * * *